US009777308B2

(12) United States Patent
Knebel et al.

(10) Patent No.: US 9,777,308 B2
(45) Date of Patent: Oct. 3, 2017

(54) DEVICE FOR ANALYZING THE EFFECT OF A GASEOUS MEDIUM ON A BIOLOGICAL TEST SYSTEM USING AN EXTRACELLULAR METABOLIZATION SYSTEM

(71) Applicant: Fraunhofer-Gesellschaft zur Foerderung der angewandten Forschung e.V., Munich (DE)

(72) Inventors: Jan Knebel, Hannover (DE); Detlef Ritter, Hannover (DE)

(73) Assignee: Fraunhofer-Gesellschaft zur Foerderung der angewandten Forschung e.V., Munich (DE)

( * ) Notice: Subject to any disclaimer, the term of this patent is extended or adjusted under 35 U.S.C. 154(b) by 221 days.

(21) Appl. No.: 13/835,640

(22) Filed: Mar. 15, 2013

(65) Prior Publication Data

US 2013/0267014 A1 Oct. 10, 2013

Related U.S. Application Data

(62) Division of application No. 12/452,154, filed as application No. PCT/DE2008/001007 on Jun. 16, 2008, now Pat. No. 8,426,157.

(30) Foreign Application Priority Data

Jun. 29, 2007 (DE) .................. 10 2007 030 413

(51) Int. Cl.
*C12M 1/34* (2006.01)
*C12Q 1/02* (2006.01)
(Continued)

(52) U.S. Cl.
CPC .............. *C12Q 1/02* (2013.01); *C12M 25/04* (2013.01); *C12M 41/46* (2013.01); *G01N 33/5008* (2013.01); *G01N 33/5014* (2013.01)

(58) Field of Classification Search
CPC ...... C12M 23/34; C12M 25/04; C12M 41/46; C12Q 1/02; C12Q 1/025; G01N 33/5008; G01N 33/5014
(Continued)

(56) References Cited

U.S. PATENT DOCUMENTS 6,164,287 A * 12/2000 White .................. A24F 47/008
131/194
6,943,009 B2 * 9/2005 Lacey et al. ............... 435/297.5
(Continued)

FOREIGN PATENT DOCUMENTS

DE 195 26 533 1/1997
DE 198 01 763 7/1999
(Continued)

OTHER PUBLICATIONS

International Search Report of PCT/DE2008/001007, mailed on Jan. 26, 2009.
(Continued)

*Primary Examiner* — William H Beisner
(74) *Attorney, Agent, or Firm* — Collard & Roe, P.C.

(57) ABSTRACT

The invention relates to a method for analyzing the effect of a gaseous medium on a biological test system using an extracellular metabolization system. The method consists of the following steps: a biological test sample is cultivated on a permeable carrier, the gaseous medium is guided over the surface of the biological test system in order to form an exposition atmosphere over the biological test system, the extracellular metabolization system is added to a conservation medium and the permeable carrier is brought into contact with a conservation medium that comprises the extracellular metabolization system below the permeable carrier, in such a manner that the extracellular metabolization system only passes through the permeable carrier and
(Continued)

that the biological test system is not submerged by the conservation medium containing the extracellular metabolization system.

9 Claims, 2 Drawing Sheets

(51) Int. Cl.
    *C12M 1/12*     (2006.01)
    *G01N 33/50*     (2006.01)

(58) Field of Classification Search
    USPC .................................................... 435/297.5
    See application file for complete search history.

(56) References Cited

U.S. PATENT DOCUMENTS

| | | | |
|---|---|---|---|
| 2005/0170499 A1* | 8/2005 | Mohr ..................... | C12M 23/10 435/289.1 |
| 2006/0099706 A1 | 5/2006 | Massey et al. | |
| 2007/0166817 A1* | 7/2007 | Wilkes .................. | C12M 25/04 435/297.5 |

FOREIGN PATENT DOCUMENTS

| | | |
|---|---|---|
| DE | 198 11 735 | 9/1999 |
| DE | 100 14 057 | 10/2001 |
| EP | 1431746 A1 * | 6/2004 |
| JP | 2002-101897 A | 4/2002 |
| WO | WO 03/100417 | 12/2003 |

OTHER PUBLICATIONS

English translation of International Preliminary Report on Patentability and Written Opinion of the International Searching Authority of PCT/DE2008/001007, issued on Jan. 19, 2010.

Aufderheide M. et al., A method for in vitro analysis of the biological activity of complex mixtures such as sidestream cigarette smoke, Exp Toxic Pathol., 2001, vol. 53, pp. 141-152.

Aiub C.A.F. et al., Standardization of conditions for the metabolic activation of N-nitrosodiethylamine in mutagenicity tests, Genetics and Molecular research (Online journal), Jun. 9, 2004, vol. 3, No. 2, pp. 264-272.

Aufderheide M. et al., A modified CULTEX® system for the direct exposure of bacteria to inhalable substances, Exp. Toxic. Pathol., 2004, vol. 55, pp. 451-454.

Pariselli F. et al., Dynamic in-vitro Exposure of Human Derived Cells to Indoor Priority Pollutants, Institute for Health and Consumer Protection, 2006, pp. 1-34.

Ritter, D. et al., "In vitro exposure of isolated cells to native gaseous compounds—Development and validation of an optimized system for human lung cells," Experimental and Toxicology Pathology, Jena, Germany, vol. 53, No. 5, Jan. 2001, pp. 373-386, XP-004956294. (ISR).

Aufderheide, M. et al., "A modified Ames assay reveals the mutagenicity of native cigarette mainstream smoke and its gas vapour phase," Experimental and Toxicology Pathology: Official Journal of the Gesellschaft für Toxikologische Pathologie, 2007, vol. 58, No. 6, Jun. 2007, pp. 383-392, XP-002502237. (ISR).

Knebel et al., "Exposure of human lung cells to native diesel motor exhaust—development of an optimized in vitro test strategy," Toxicology in Vitro 16 (2002), pp. 185-192.

M. J. Gómez-Lechón et al.,"Hepatocytes—the choice to investigate drug metabolism and toxicity in man: In vitro variability as a reflection of in vivo," Chemico-Biological Interactions, (2006), doi: 10.1016/j.cbi.2006.10.013, pp. 1-21. (Spec, p. 2).

Aden et al., "Controlled synthesis of HBsAg in a differentiated human liver carcinoma-derived cell line," Nature, vol. 282, Dec. 6, 1979, pp. 615-616. (Spec, p. 2).

A. Townsend et al., "Modeling the metabolic competency of glutathione S-transferases using genetically modified cell lines," Toxicology 181-182 (2002) pp. 265-269. (Spec, pp. 2-3).

N. Krebsfaenger et al., "V79 Chinese Hamster Cells Genetically for Polymorphic Cytochrome P450 2D6 and their Predictive Value for Humans," ALTEX 20, Mar. 2003, pp. 143-154. (Spec, p. 3).

S. Bremer et al., "Detection of the Embryotoxic Potential of Cyclophosamide by Using a Combined System of Metabolic Competent Cells and Embryonic Stem Cells," ATLA 30, 2002, pp. 77-85. (Spec, p. 3).

D. S. Pushparajah et al., "Evaluation of the precision-cut liver and lung slice systems for the study of induction of CYP1, epoxide hydrolase and glutathione S-transferase activities," Toxicology 231 (2007) pp. 68-80. (Spec, p. 3).

"OECD Guideline for the Testing of Chemicals" No. 473, adopted: Jul. 21, 1997, pp. 1-10. (Spec, p. 3 and 7).

Dorothy M. Maron and Bruce N. Ames, "Revised methods for the Salmonella mutagenicity test," Mutation Research, 113 (1983) pp. 173-215. (Spec, p. 22).

Rees et al., Abstract of "Optimization of metabolic activation for four mutagens in a bacterial, fungal and two mammalian cell mutagenesis assays.", Mutagenesis, Sep. 1989; 4(5), pp. 335-342.

Gletten et al., "In Vitro Metabolic Activation of Chemical Mutagens I. Development of an In Vitro Mutagenicity Assay Using Liver Microsomal Enzymes for the Activation of Dimethylnitrosamine to a Mutagen", Mutation Research, 28(1975), pp. 113-122.

Amacher et al., Abstract of "The effect of liver postmitochondrial fraction concentration from Aroclor 1254-treated rats on promutagen activation in L5178Y cells.", Mutation Research, Apr. 1982; 97(2), pp. 131-137.

Mehnert et al., Abstract of "Differences in the induction of SCEs between human whole blood cultures and purified lymphocyte cultures and the effect of an S9 mix." Mutation Research, Dec. 1984; 130(6), pp. 403-410.

Thompson et al., Abstract of "Comparative genotoxic effects of the cooked-food-related mutagens Trp-P-2 and IQ in bacteria and cultured mammalian cells." Mutation Research, May-Jun. 1983; 117(3-4), pp. 243-257.

Kirkland et al., "Testing Strategies in mutagenicity and genetic toxicology: An appraisal of the guidelines of the European Scientific Committee for Cosmetics and Non-Food Products for the evaluation of hair dyes", Mutation Research, 588 (2005), pp. 88-105.

Wilson et al., "Characterisation of the toxic metabolite(s) of naphthalene", Toxicology, 114 (1986) pp. 233-242.

Wilson et al., Abstract of "Evaluation of the generation of genotoxic and cytotoxic metabolites of benzo[a]pyrene, aflatoxin B1, naphthalene and tamoxifen using human liver microsomes and human lymphocytes." Hum. Exp. Toxicol., Jun. 1995; 14(6), pp. 507-515, Databank PubMed at NCBI, http://www.ncbi.nlm.nih.gov.

Aufderheide et al. (2003). "An improved in vitro model for testing the pulmonary toxicity of complex mixtures such as cigarette smoke." Exp Toxic Pathol; 55: 51-57.

Takamura et al. (2005). "Toxicity of Diesel exhaust gases and their evaluation procedures." Petrotech, vol. 28, No. 5, pp. 322-326, with English abstract attached.

OECD Guideline for the Testing of Chemicals Jul. 21, 1997 (total of 10 pages).

* cited by examiner

DEVICE FOR ANALYZING THE EFFECT OF A GASEOUS MEDIUM ON A BIOLOGICAL TEST SYSTEM USING AN EXTRACELLULAR METABOLIZATION SYSTEM

CROSS REFERENCE TO RELATED APPLICATIONS

This application is a divisional of and Applicant claims priority under 35 U.S.C. §§120 and 121 of U.S. application Ser. No. 12/452,154 filed on Dec. 17, 2009, which application is a national stage application under 35 U.S.C. §371 of PCT Application No. PCT/DE2008/001007 filed on Jun. 16, 2008, which claims priority under 35 U.S.C. §119 from German Patent Application No. 10 2007 030 413.9 filed on Jun. 29, 2007, the disclosures of each of which are hereby incorporated by reference. A certified copy of priority German Patent Application No. 10 2007 030 413.9 is contained in parent U.S. application Ser. No. 12/452,154. The International Application under PCT article 21(2) was not published in English.

BACKGROUND OF THE INVENTION

1. Field of the Invention

The invention relates to a method for analyzing the effect of a gaseous medium on a biological test system using an extracellular metabolization system, and to a device for carrying out the method.

2. Description of the Related Art

Known in the art is to expose cellular test systems in the form of eukaryote cultures, in particular cell lines, primary cells, biopsies, lavages, isolates, PCLS and the like, to ex-vivo airborne substances of a native or artificial type so as to analyze the biological effect of these substances. The eukaryote cultures are here exposed to an artificial or natural test atmosphere, also referred to as exposition atmosphere.

Since the intermediate metabolic products of the specified airborne substances are often the first to become biologically active, a biological effect of the test atmosphere in the cellular test system only becomes detectable after having been able to form the specified intermediate metabolic products during a metabolization of the specified airborne substances.

Cited below are examples of cellular test systems in which an intracellular metabolization capacity was ruled out or confirmed:

(a) Isolates of primary cells with rather varyingly defined metabolizing capabilities/capacities that differ as a function of the respective isolation technique and isolation batch (e.g., hepatocytes of rat livers or from human biopsies; M. J. Gomez-Lechon et al., Hepatocytes—the choice to investigate drug metabolism and toxicity in man: Ir. vitro variability as a reflection of in vivo, Chemico-Biol. Int. (2006), dol: 10.1016/j.cbj.2006.19.013).

(b) Immortalized hepatocyte cell lines that can have a varying metabolizing capability/capacity depending on subpopulation (e.g., the human hepatoma cell line HepG2; Aden et al. 1979).

(c) Genetically altered cell systems (e.g., cell lines derived from V79 with defined expression of specific cytochrome P-450 forms; A. Townsend et al., Modeling the metabloc competency of gutathione S-transferases using genetically modified cell lines, Toxicology 181-182 (2002) 265-269; N. Krebsfaenger et al., V79 Chinese Hamster Cells Genetically for Polymorphic Cytochrome P450 2D6 and their Predictive Value for Humans, ALTEX 20, 3/03, 143-154).

(d) Cocultures of metabolically competent cells and non-metabolizing cells of the primary target tissue of the noxae (S. Bremer et al., Detection of the Embryotoxic Potential of Cyclophosamide by Using a Combined System of Metabolic Competent Cells and Embryonic Stem Cells, ATLA 30, 77-85, 2002).

(e) Tissue sections (D. S. Pushparajah et al., Evaluation of the precision-cut liver and lung slice systems for the study of induction of CYP1, epoxide hydrolase and glutathione S-transferase activities, Toxicology 231 (2007) 68-80).

The complexity of culture processes along with the availability and reproducibility of metabolization efficiency can be disadvantageous relative to these cellular test systems with intracellular metabolization systems.

The aforementioned cellular test systems with intracellular metabolization system also do not compulsorily satisfy the requirements imposed by various internationally test provisions, for example the "OECD Guideline for the Testing of Chemicals" No. 473, which mandate the presence of a sufficiently efficient metabolization system.

In order to satisfy these test requirements, it is known that use can be made of cellular test systems without intracellular metabolization or cellular test systems in which the efficiency of intracellular metabolization has not been verified, which are exposed in flat-bottomed culture flasks or round culture flasks, so-called roller bottles. The cellular test system is here coated with a mixture of conservation medium and an extracellular metabolization system, and the test atmosphere is continuously passed through the flask. In order to thoroughly mix the conservation medium, extracellular metabolization system and test atmosphere, the culture flasks are shaken, tilted or rotated.

The disadvantage to this method is that no direct and defined contact is possible between the test atmosphere and cellular test system. Therefore, the result is imbued with less sensitivity and specificity, as well as with the absence of an exact dosimetry.

SUMMARY OF THE INVENTION

Proceeding from this prior art, the object of the invention is to provide an alternative method with a high sensitivity and selectivity to analyze the effect of a gaseous medium on a biological test system using an extracellular metabolization system, as well as a device for carrying out this method.

This object is achieved by a method for analyzing the effect of a gaseous medium on a biological test system using an extracellular metabolization system according to one aspect of the invention, as well as by an exposition device according to another aspect of the invention. Further developments and advantageous embodiments of the invention are discussed below.

The method according to the invention for analyzing the effect of a gaseous medium on a biological test system using an extracellular metabolization system encompasses the following procedural steps:

Cultivating a biological test system on a permeable carrier;

Guiding the gaseous medium over the surface of the biological test system to form an exposition atmosphere over the biological test system;

Adding the extracellular metabolization system to a conservation medium;

Positioning the conservation medium with extracellular metabolization system under the permeable carrier with contact to the permeable carrier, in such a way that the extracellular metabolization system only passes through the permeable carrier, while the biological test system is not flooded with extracellular metabolization system.

The method according to the invention makes it possible to analyze the effect of a gaseous medium on a biological test system with a high sensitivity and selectivity using an extracellular metabolization system.

The method according to the invention satisfies the following conditions that are recognized as essential to the invention, responsible for the high sensitivity and selectivity of the method, and to be observed simultaneously during exposition of the biological test system in the exposition atmosphere:

a) A direct and unobstructed contact is established between the exposition atmosphere and biological test system;
b) Contact is established between the exposition atmosphere and the extracellular metabolization system;
c) The reaction products of the metabolization reactions of the exposition atmosphere with the extracellular metabolization system are made accessible to the biological test system.
d) The conservation medium is made accessible to the biological test system.
e) The vitality of the biological test system is assured.

Regardless of whether the biological test system exhibits intracellular metabolization capabilities or the whether intracellular metabolization capabilities are completely absent in the biological test, not pronounced enough, not sufficiently reproducible or too vaguely defined, the method according to the invention uses a defined, extracellular metabolization system to ensure the metabolization capability.

The important factor is that the boundary layer comprised of a permeable carrier with biological test system exposed thereupon quasi physically separates the compartments "exposition atmosphere" and "conservation medium with extracellular metabolization system" from each other, so that the conservation medium with extracellular metabolization system can only pass through the permeable carrier in the manner prescribed by the invention.

In terms of the invention, a conservation medium is here and below also referred to as a culture medium, also referred to as a nutrient medium, with or without additives or a saline solution.

The gaseous medium as defined in the invention can be present as a pure gas or gas mixture, i.e., all substances (atoms, molecules, etc.) contained therein exist in the gaseous phase, and/or it can also serve as a carrier for solids and/or liquids. In particular, aerosols, atomized liquids, small liquid droplets (e.g., plant protective agents as a spray, etc.), suspended particles, solid particles (e.g., wood dust, etc.), gaseous suspensions, atomized suspensions or emulsions can be incorporated in the carrier gas as substances to be carried.

The method according to the invention makes it possible to easily analyze the biological effect of gaseous media of all kinds in routine applications using biological test systems that might under certain conditions not have an independent metabolization capacity in a safe manner, i.e., while retaining vitality, ensuring a high sensitivity for the method due to intensive contact between the exposition atmosphere and both the biological test system and extracellular metabolization system, and in particular observing diverse international test provisions, for example the OECD 473 known by the expert.

In addition, the method according to the invention enables the use of individually fabricated compositions of diverse external metabolization systems known to the expert, for example with cytochromes of laboratory animals or humans that can be specifically tailored to various specific metabolic characteristics of a biological test system.

The invention preferably involves the use of a permeable carrier designed in such a way as to be suitable for accommodating the biological test system on the one hand, and enable a separation of the gaseous phase, meaning the exposition atmosphere, from the liquid phase, meaning the conservation medium with extracellular metabolization system, on the other. Therefore, the pore size and pore density of the permeable carrier can vary as a function of the type of biological test system and the type and viscosity of the conservation medium.

A microporous membrane is preferably used as the permeable carrier. A gel is preferably used as the permeable carrier. To accommodate the biological test system, a culture flask can also be provided, for example a commercially available, so-called cell culture insert, wherein the permeable carrier constitutes the floor membrane of the culture flask.

A further development of the invention is characterized by the following additional procedural step:

Regulating the passage of the extracellular metabolization system added to the conservation medium through the permeable carrier by prescribing a specific pressure that acts on the conservation medium with extracellular metabolization system.

It is further provided that the pressure acting on the conservation medium with extracellular metabolism system is selected in such a way that the extracellular metabolization system passes through the permeable carrier, but the biological test system is not flooded by the conservation medium with extracellular metabolization system.

One advantageous embodiment of the invention is characterized by the following additional procedural step:

Regulating the evaporation rate over the biological test system by prescribing a specific temperature in direct proximity to the biological test system and/or prescribing a specific flow rate of the gaseous medium steaming over the surface of the biological test system.

Controlling the temperature, preferably in direct proximity to the biological test system, makes it possible to regulate the evaporation rate of the conservation medium with extracellular metabolization system passing through the permeable membrane, so as to prevent the biological test system from drying out, and hence dying off.

The evaporation rate also depends on the moisture content of the gaseous medium. The flow rate of the gaseous medium over the biological test system must be correspondingly regulated or controlled.

The regulation and control of these two aforementioned parameters along with the pressure acting on the conservation medium with extracellular metabolization system establishes defined conditions for analyzing the effect of a gaseous medium on a biological test system using an extracellular metabolization system.

The invention also relates to an exposition device for carrying out the method. The exposition device comprises:

At least one permeable carrier, on which a biological test system is cultured;

At least one feed system, which can route a gaseous medium over the surface of the biological test system to form an exposition atmosphere above the biological test system;

A delivery system that contains a conservation medium with extracellular metabolization system and is designed in such a way that the conservation medium with extracellular metabolization system is in direct contact with the lower side of the permeable carrier, wherein The permeable carrier is designed and situated inside the exposition device in such a way that the latter physically separates the conservation medium with extracellular metabolization system from the exposition atmosphere, wherein The conservation medium with extracellular metabolization system can only be forced through the permeable carrier in a defined manner by means of a prescribed pressure, specifically in such a way that the conservation medium with extracellular metabolization system passes through the permeable carrier, but the biological test system is not flooded by the conservation medium with extracellular metabolization system.

The feed system comprises all devices suitable for routing the gaseous medium over the surface of the biological test system to form an exposition atmosphere above the biological test system. Such a device is known from DE 100 14 057 A1, for example. The disclosure of this patent application is hereby completely incorporated into the present application by reference.

The feed system preferably also encompasses all devices that use their structural design to realize the feeding of the gaseous medium in a special way, for example with a hyperbolic interior profile for the targeted separation of aerosol droplets.

The feed system further preferably also encompasses devices for electrostatically separating particles or droplets and/or a charging device. Such devices are known from DE 195 26 533 A1, for example. The disclosure of this patent application is hereby also completely incorporated into the present application by reference.

In a further development of the invention, the delivery system is sealed off from the feed system and exposition atmosphere, and the conservation medium with extracellular metabolization system can only come into contact with the exposition atmosphere through the permeable carrier.

According to the invention, the prescribed pressure can be set hydrostatically, or via at least one pump or some other pressure-generating means.

In a further development of the invention, the delivery system is designed in such a way that the conservation medium with extracellular metabolization system contained therein remains in the delivery system for the duration of the analysis.

The permeable carrier is preferably designed in such a way as to enable the accommodation of the biological test system on the one hand, and a separation of the gaseous phase, meaning the exposition atmosphere, from the liquid phase, meaning the conservation medium with extracellular metabolization system, on the other. The latter depends in particular on the type of biological test system, as well as on the type and viscosity of the conservation medium with extracellular metabolization system.

In one advantageous embodiment of the invention, a discharge system is provided, with which the exposition atmosphere can be removed from the exposition device after residing therein for a predetermined period.

It is further provided that the feed and/or discharge system is designed in such a way that the gaseous medium can be relayed in controlled fashion through the exposition device by means of an underpressure system or an overpressure system.

The preferred means for continuously generating a corresponding pressure differential between the feed and/or discharge device is a pump, which is situated in the discharge system from the standpoint of flow. To advantageously adjust the flow rate of the medium, it is especially preferred that it be possible to control the pump in terms of its pumping capacity.

In a further development of the invention, a removal system is best provided with which the conservation medium with extracellular metabolization system can be removed from the exposition device after residing therein for a prescribed retention period.

The delivery and removal system is preferably designed in such a way that the conservation medium with extracellular metabolization system contained therein is routed through the delivery and removal system in a continuous or pulsating flow, wherein at least one pump is preferably provided for this purpose.

One advantageous embodiment of the invention provides at least one heating device, with which the temperature of the exposition device can be entirely or partially controlled.

Controlling the temperature, preferably in direct proximity to the biological test system, makes it possible to regulate the evaporation rate of the conservation medium with extracellular metabolization system passing through the permeable membrane, so as to prevent the biological test system from drying out, and hence dying off.

The evaporation rate also depends on the moisture content in the gaseous medium. The flow rate of the gaseous medium over the biological test system must be correspondingly regulated or controlled.

In another advantageous embodiment of the invention, the exposition device according to the invention correspondingly also encompasses a device for regulating and controlling the flow rate of the gaseous medium over the biological test system.

The regulation and control of these two aforementioned parameters along with the necessary pressure acting on the conservation medium with extracellular metabolization system establishes defined conditions for analyzing the effect of a gaseous medium on a biological test system using an extracellular metabolization system.

The used biological test system is preferably either a eukaryote culture, especially preferably cell lines, primary cell isolates, tissue sections, reconstructed tissue such as cocultures, or genetically altered cells, or a prokaryote culture. Such a biological test system is preferably used in the aforementioned method according to the invention.

A further development of the invention provides that the exposition device be combined with a cell-based sensor array.

The term “cell-based sensor array” is understood as encompassing all devices suitable for analyzing the used biological test systems while positioning them on the permeable carrier in the exposition device.

In particular, this can be realized in the form of an online measurement, or an analytical system able to read out a measured value within shorter or longer time intervals.

For example, cell-based sensor arrays can be realized for end points based on the use of a fluorescence or luminescence measurement. To this end, the biological test system is provided with a fluorophore, the properties of which are correlated with the cellular condition, and can hence image that latter via fluorescence analysis with respect to certain aspects, for example by dyeing the cells with $H_2DCFDA$ to detect intracellular radical formation. Suitable optics, for example fiber optic, and an external light source and detector along with a controller and measuring sensor can then be used for light stimulation—i.e., excitation—and emission measurement—i.e., emission—directly on the biological test system on the membrane. For example, a corresponding arrangement can be provided for analyzing luminescence phenomena, e.g., in conjunction with expression analyses, such as reporter gene assays.

Cell-based sensor arrays can also be realized via electrical or electrochemical measurements, for example, in particular in the form of an electrical resistance measurement, or TEER, trans-epithelial electrical resistance, or in the form of an impedance measurement.

Another configuration for cell-based sensor arrays can involve an arrangement suitable for analyzing substances issued by the cell, for example enzymes like lactate dehydrogenase or cytokines, quantitatively or qualitatively in the conservation medium.

In particular, these arrangements are suited for permitting an analysis during an exposition process.

The invention further relates to the use of the method or the exposition device for exposing at least one biological test system in cigarette smoke or the like or in exhaust gases, preferably in automobile exhaust gases or industrial exhaust gases.

The invention also relates to the use of the method or the exposition device for analyzing environmental atmospheres, workplace atmospheres or room atmospheres.

The invention additionally relates to the use of the method or the exposition device for analyzing the effect of a gaseous medium on a biological test system in the area of product safety, user protection, pharmaceutical development production monitoring or medical technology.

The invention further relates to the use of the method or the exposition device for analyzing the effect of a gaseous medium on a biological test system while observing regulatory guidelines, preferably OECD guidelines.

One preferred application of the method according to one aspect of the invention or the exposition device according to another aspect of the invention involves the approval-relevant testing of technically manufactured atmospheres, for example gas preparations or mixtures, the manufacture and marketing of which require official approval under laws governing chemicals, and the safety of which must be demonstrated under EU law in tests that do not involve the use of test animals if at all possible.

The invention further relates to using the method or the exposition device for analyzing the effect of a gaseous medium on a biological test system specifically for analyzing toxicological effects, genotoxic effects, immunomodulatory or immunotoxic effects or other biologically or toxicologically relevant cellular changes.

BRIEF DESCRIPTION OF THE DRAWINGS

An exemplary embodiment depicted in the drawing will be used below to explain the invention. Shown on.

DETAILED DESCRIPTION OF PREFERRED EMBODIMENTS

Figure 1:
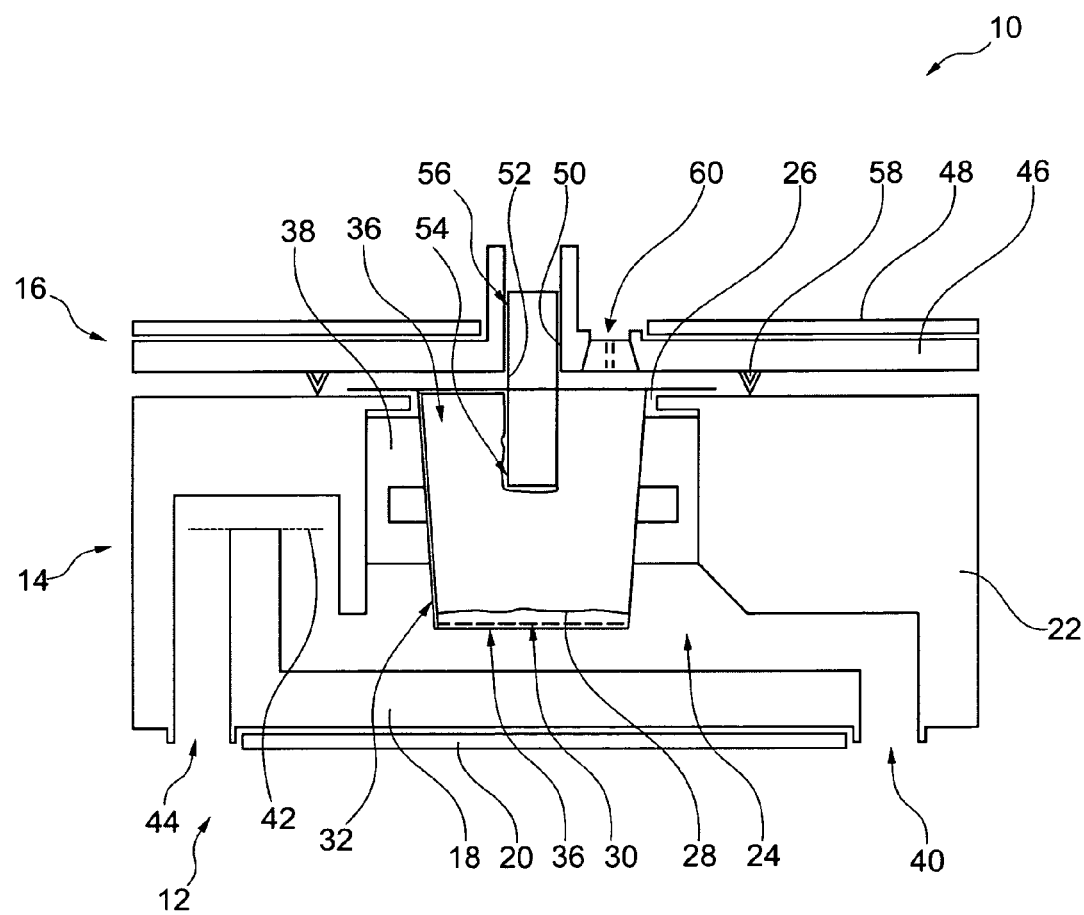
FIG. 1 is a schematic partial view of an exposition device suitable for carrying out the method according to the invention, and on FIG. 2 is a schematic setup for a possible analysis on the effect of n-butane on a biological test system using an extracellular metabolization system.
Figure 2:
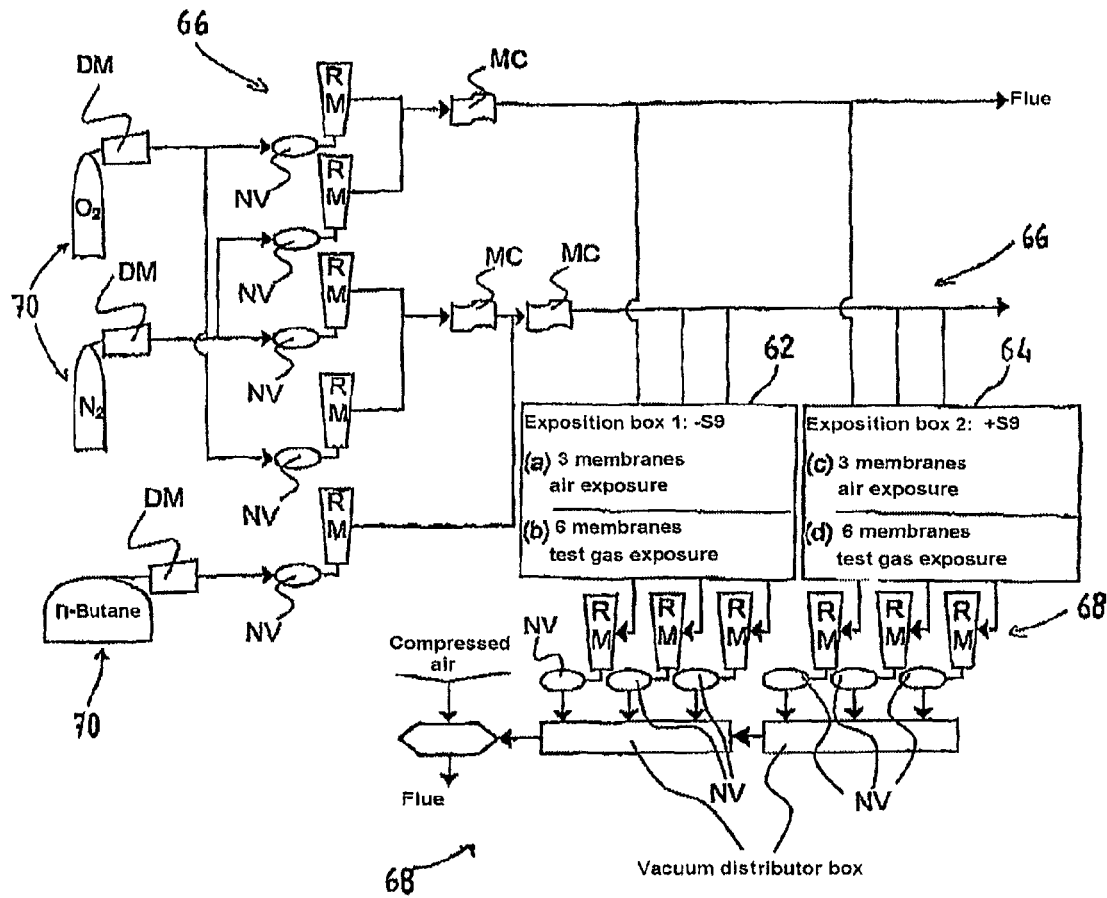

The exposition device 10 shown schematically in a partial view on FIG. 1 can also be transported in field tests, and exhibits a substructure 12, a central structure 14 arranged on the substructure, and a superstructure 16 arranged on the central structure 14.

The substructure 12 is designed as a tub 18, which preferably consists of a polycarbonate. Situated below the tub 18 is an electrical heater 20, which makes it possible to control the temperature of the exposition device 10.

Also provided are a supply tank (not shown here) for holding a conservation medium with metabolization system added according to the invention, and a hose pump (not shown here) for conveying the conservation medium with metabolization system from the supply tank into the tub 18.

The tub 18 of the substructure 12 is tightly joined with a plate 22 of the central structure 14 with the formation of at least one cavity 24, to which the conservation medium with metabolization system can be routed. The plate 22 preferably consists of a polycarbonate.

Let it be noted that the terms tub 18 and plate 22 must not be construed as meaning that the tub 18 always exhibits a floor with pulled up walls and the plate 22 is only flat in design. The tub 18 can essentially also be flat in design, and the plate 22 can exhibit pulled down walls. This is shown by example on FIG. 1. Various transitional stages between the tub 18 and plate 22 with various profiles are also possible.

The plate 22 further exhibits at least one receiving means, in the present case in the form of a hole 26, for accommodating a permeable carrier 30 provided with a biological test system 28, here in the form of a culture flask 32.

The culture flask 32 shown on FIG. 1 is shaped like a beaker with a circular cross section, wherein the diameter conically tapers from the beaker opening 34 to the beaker floor 36. The beaker floor 36 consists of a porous plastic material, for example polyethylene terephthalate. The culture flask 32 represents a liquid-permeable carrying structure for the permeable carrier 30, in particular a microporous membrane 30, which can be made out of various plastic materials depending on the requirement of the cells to be cultivated, e.g., polyethylene terephthalate as well. The microporous membrane 30 here carries the biological test system 28.

The beaker floor 36 of each culture flask 32 projects into the cavity 24 formed by the tub 18 and late 22. The beaker opening 34 is located above the plate 22.

It is important that the culture flask 32 accommodated in each hole 26 of the plate 22 be sealed on the outer beaker wall relative to the plate 22 by means of a sealant 38, preferably by means of a silicone bead. This is essential to the invention, since only in this way can it be ensured that the conservation medium with metabolization system can only pass through the microporous membrane 30 and come into contact with the exposition atmosphere. This prevents the conservation medium with metabolization system from being pressed upward passing by the culture flask 32, and then disadvantageously getting into the beaker opening 34 from above, and hence into the culture flask 32, or flooding the plate 22.

The conservation medium with metabolization system is preferably supplied via an inlet opening 40 in the floor of the tub 18. The conservation medium with metabolization system then fills the cavity 24 between the tub 18 and plate 22, and comes into contact with the microporous membrane 30 on its 30 lower side. In order to now be able to press the metabolization system in the conservation medium through the microporous membrane 30 to the biological test system 28 cultivated on the membrane 30, pressure must be exerted on the conservation medium with metabolization system. This takes place hydrostatically in the simplest case. To this end, the conservation medium with metabolization system is pumped via the hose pump to a level 42 within the cavity 24 lying above the beaker floor 36, meaning above the microporous membrane 30. By preferably shifting the culture flask 32, i.e., changing the level of the permeable carrier 30, the pressure can also be changed.

The necessary level or necessary pressure required to press the metabolization system with conservation medium through the microporous membrane 30 according to the invention depends in particular on the type of microporous membrane 30, meaning on the pore size and pore density, and on the used conservation medium with extracellular metabolization system. The necessary pressure is hence determined empirically.

The exposition device 10 preferably exhibits an outlet opening 44 in the floor of the tub 18 through which the spent conservation medium with extracellular metabolization system can be discharged from the exposition device 10, in this case by the conservation medium with metabolization system exceeding the specified level 42.

Situated on the plate 22 of the central structure 14 is a superstructure 16 that encompasses a cover 46 with pulled down walls.

Another heater 48 for controlling the temperature of the exposition device 10 can be provided on the cover 46.

Provided within the cover 46 is at least one hole, which is positioned over a culture flask 32 accommodated in the plate 22.

Situated in this hole 50 is a flow inlet pipe 52 for the gaseous medium, one end 54 of which projects directly into the culture flask 32, wherein the end 54 is positioned just above the biological test system 28. The other end 56 of the flow inlet pipe 52 is positioned outside the cover 46. The flow inlet pipe 52 is outwardly sealed relative to the cover 46.

Located between the plate 22 and cover 46 around each culture flask 18 is another seal, preferably in the form of a gasket 58.

Situated within the gasket 58 in the cover 48 still in direct proximity to the aforementioned hole 50 is an outlet opening 60 for the gaseous medium.

The outlet opening 60 is preferably connected with a vacuum pump (not shown here) to aspirate a gaseous medium through the flow inlet pipe 52 on the surface of the biological test system 28 and subsequently through the outlet opening 60.

The gaseous medium can stem from the outside atmosphere when using the exposition device 10 in a field test. This makes it possible to analyze the effects of various naturally occurring atmospheres on a biological test system 28, for example.

Naturally, it is also possible to allow the gaseous medium to be analyzed through the flow inlet pipe 52 without a vacuum pump. To this end, the flow guiding pipe 55 is connected with a pressurized supply flask (not shown here).

It is only important that there be a pressure differential between the flow inlet pipe 52 and outlet opening 60, so that the gaseous medium can continuously flow over the surface of the biological test system 28 and, according to the invention, over the metabolization system.

The hose pump is serviced via a controlling/regulating unit (not shown here), so as to supply the biological test system 28 in the culture flask 32 with the conservation medium on the one hand, and to enable the metabolization system added to the conservation medium to pass through the permeable carrier 30 according to the invention on the other, specifically in such a way that the conservation medium with metabolization system is pumped via the hose pump to a level 42 within the cavity 24 lying above the beaker floor 36, meaning above the microporous membrane 30. The pressure acting hydrostatically on the conservation medium with metabolization system presses the metabolization system through the permeable carrier 30 only to such an extent that the biological test system 28 is not flooded by the conservation medium with metabolization system.

Therefore, the hose pump is provided not just to pump conservation medium into the cavity 24 to provide the biological test system 28, but rather also ensures that the conservation medium with metabolization system in the cavity 24 between the tub 18 and plate 22 is exposed to pressure in such a way that the metabolization system can be pressed by the present microporous membrane 30 without the conservation medium with metabolization system flooding the biological test system 28. A submersion of the biological test system 28 is here entirely undesired according to the invention.

In order to reliably achieve a situation where the metabolization system comes in direct proximity or into contact with the biological test system 28, but the latter is not flooded by the conservation medium with metabolization system, it may make sense to use a sensor (not shown here) for determining the flow of conservation medium with metabolization system through the microporous membrane 30, which is connected with the controlling/regulating unit of the hose pump, and relays corresponding signals to the controlling/regulating unit for activating/deactivating the hose pump.

Temperature sensors (not shown here) can further be provided on or within the cavity 24 filled with conservation medium and metabolization system, specifically for controlling the temperature of the conservation medium with metabolization system by means of the aforementioned heaters 20, 48.

FIG. 2 shows a schematic setup for a possible analysis of the effect of n-butane on a biological test system using an extracellular metabolization system.

Two exposition systems 62 and 64, here marked exposition box 1 and exposition box 2, were used for the analysis.

Each exposition device 62, 64 exhibits nine permeable carriers in the form of microporous membranes. Lung cells of the V-79 line are sued as the biological test system. These were cultivated biphasically, i.e., on the air-liquid interface, on the microporous membrane beforehand, and then introduced into the respective exposition device 62, 64, as shown on FIG. 1.

Each exposition device 62, 64 is filled with a conservation medium, specifically with a culture medium, wherein only the culture medium of the exposition device 64 has received an extracellular metabolization system, specifically a 3% S9 mix.

An S9 mix is known to the expert, but is also described, for example, in "D. M. Maron and B. N. Ames, Revised Methods for the *Salmonella* Mutagenicity Test, Mutation Research, 113 (1983) 173-215".

Both the conservation medium without extracellular metabolization system, meaning without S9 mix, and the conservation medium with extracellular metabolization system, meaning with S9 mix, are basally in contact with each microporous membrane according to the inventive setup, and are each separated by the latter from the exposition atmosphere, which apically reaches the microporous membrane.

The conservation medium without or with extracellular metabolization system is continuously and reproducibly temperature controlled, and acts on the microporous membranes from below with a prescribed pressure as a function of the existing/absent S9 component in the conservation medium.

The biological test systems situated on the microporous membranes in these exposition devices 62, 64 are transported from the cell culture laboratory to an exposition site remote from the laboratory.

The exposition devices 62, 64 are there connected with the feed 66 and discharge 68 systems of the test 70 and reference atmosphere 72.

The test atmosphere n-butane 70 is diluted with pure air or a mixture of nitrogen and oxygen. The end concentration contains 20.5% oxygen.

Exposure to a pure air control takes place parallel and simultaneously, accompanied by an exposure of biological test systems with and without added S9 mix in the culture medium.

The constant supply of test and reference atmosphere 70, 72 to the biological test systems at a flow rate of 10 ml/min/cm$^2$ is ensured over the exposition period by regulating the flow rate in an underpressure system. The test or reference atmosphere 70, 72 is guided over the biological test system, meaning the cell layers.

The exposition time measures at least 3 hours.

The exposition devices 62, 63 are then separated from their feed 66 and discharge 68 systems and transported back into the cell culture laboratory.

The microporous membranes with their biological test systems are removed.

The preparation of the biological test systems, meaning the V79 cells, is followed by: an analysis of the toxicity by means of a neutral red assay; an examination of the lactate dehydrogenase release; an analysis of apoptosis by means of annexin-V-assay; an examination of oxidative stress via an analysis of the intracellular glutathione status; an examination of genotoxicity by means of micronucleus and COMET assay.

REFERENCE LIST

Part of the Specification

10 Exposition device
12 Substructure
13 Central structure
16 Superstructure
18 Tub
20 Heater
22 Plate
24 Cavity
26 Hole
28 Biological test medium
30 Permeable carrier
32 Culture flask
34 Beaker opening
36 Beaker floor
38 Sealant
40 Inlet opening
42 Level
44 Outlet opening
46 Cover
48 Heater
50 Hole
52 Flow inlet pipe
54 End
56 End
58 Gasket ring
60 Outlet opening
62 Exposition device
64 Exposition device
66 Feed system
68 Discharge system
70 Test atmosphere
72 Reference atmosphere

What is claimed is:

1. An exposure device (10) for carrying out a method for analyzing the effect of a gaseous medium on a biological test system using an extracellular metabolization system, comprising:
   at least one permeable carrier (30), on which a biological test system (28) is cultured;
   compartments within the exposure device being physically separated from one another by the permeable carrier such that there is an upper compartment with an exposure atmosphere on one side of the permeable carrier and a lower compartment with a conservation medium with extracellular metabolization system on the other side of the permeable carrier;
   wherein the permeable carrier is designed in such a way as to enable the accommodation of the biological test system and to enable the separation of the exposure atmosphere from the conservation medium with extracellular metabolization system; wherein
   the permeable carrier (30) is disposed on the bottom (36) of a culture vessel (32) or forms this bottom (36), wherein the culture vessel (32) is disposed in an accommodation (26) of the exposure device (10), and a seal (38) is disposed between the outside wall of the culture vessel (32) and the wall of the accommodation (26), wherein
   at least one feed pipe, which can route the gaseous medium over the surface of the biological test system to form the exposure atmosphere above the biological test system (28) within the upper compartment;
   a delivery pipe (24, 40), which routes the conservation medium with extracellular metabolization system into the lower compartment, wherein
   the conservation medium with extracellular metabolization system is in direct contact with the underside of the permeable carrier (30), wherein
   the delivery pipe (24,40) and the lower compartment are sealed off from the feed pipe (52) and the upper compartment such that
   the conservation medium with extracellular metabolization system can only be forced through the permeable carrier (30) in a defined manner by means of a prescribed pressure, wherein the prescribed pressure can be set hydrostatically, or via at least one pump or some other pressure-generating means, in such a way that the conservation medium with extracellular metabolization system passes through the permeable carrier (30), but the biological test system (28) is not flooded by the conservation medium with extracellular metabolization system.

2. The exposure device according to claim 1, wherein a discharge pipe is provided, with which the exposure atmosphere can be removed from the exposure device after residing therein for a predetermined period, wherein the discharge pipe is connected with the upper compartment.

3. The exposure device according to claim 2, wherein means to generate an underpressure in the discharge pipe is provided such that the gaseous medium can be relayed in controlled fashion through the exposure device.

4. The exposure device according to claim 1, wherein means to generate an overpressure in the feed pipe is provided such that the gaseous medium can be relayed in controlled fashion through the exposure device.

5. The exposure device according to claim 1, wherein a removal pipe is provided with which the conservation medium with extracellular metabolization system can be removed from the exposure device after residing therein for a prescribed retention period, wherein the removal pipe is connected with the lower compartment.

6. The exposure device according to claim 5, wherein the delivery and removal pipe comprising at least one pump such that the conservation medium with extracellular metabolization system is routed through the delivery pipe, the lower compartment and the removal pipe in a continuous or pulsating flow.

7. The exposure device according to claim 1, wherein at least one heating device is provided, with which the temperature of the exposure device can be entirely or partially controlled.

8. The exposure device according to claim 1, wherein the biological test system is either a eukaryote culture or a prokaryote culture.

9. The exposure device according to claim 1, wherein it is combined with a cell based sensor array.

* * * * *